United States Patent [19]
Orson, Sr.

[11] Patent Number: 5,081,104
[45] Date of Patent: Jan. 14, 1992

[54] FRAGRANCE DISPENSING COMPOSITION WITH CONTROLLED EVAPORATION RATE AND AIR FRAGRANCE DISPENSER FOR DISPENSING SAME

[75] Inventor: Steven F. Orson, Sr., Wayne, N.J.

[73] Assignee: Kurary Co., Ltd., Okayama, Japan

[21] Appl. No.: 541,017

[22] Filed: Jun. 20, 1990

[51] Int. Cl.$^5$ ............................................... A61K 7/46
[52] U.S. Cl. ........................................ 512/3; 424/76.4; 239/44
[58] Field of Search ............... 512/3, 4; 424/76.4

[56] References Cited

U.S. PATENT DOCUMENTS 2,422,145  6/1947  Taylor ................................. 512/3
4,663,081  5/1987  Grimshaw et al. .................. 512/3

OTHER PUBLICATIONS

Yoshioka et al., Chem. Abst., vol 111, #102555n (1989).
Toyama, Chem. Abst., vol. 111, #156,585v (1989).
Taniguchi, Chem. Abst., vol 105, #232224r (1986), vol. 98, #149, 464K (1983).
Chem. Abst., vol. 98, #149, 464K (1983).
Hasegawa, Chem. Abst., vol 101, #78,687c (1984).

*Primary Examiner*—James H. Reamer
*Attorney, Agent, or Firm*—Sherman and Shalloway

[57] ABSTRACT

The solubility and evaporation rates of volatile fragrances, such as perfumes, in aqueous media, are improved by 3-methyl-3-methoxy butanol or an ester thereof. Homogeneous and clear aqueous solutions of as much as 20 to 30% fragrance can be achieved without incorporation of any surfactant. The aqueous fragrance solutions may be incorporated in wick type air freshener devices, which may be fan assisted.

21 Claims, No Drawings

FRAGRANCE DISPENSING COMPOSITION WITH CONTROLLED EVAPORATION RATE AND AIR FRAGRANCE DISPENSER FOR DISPENSING SAME

BACKGROUND OF THE INVENTION

1. Field of the Invention

This invention relates to an aqueous composition of a fragrance. More particularly, the invention relates to an aqueous composition of a fragrance suitable for use in an air freshener device for dispensing fragrance into the surrounding environment and which composition contains 3-methyl-3-methoxy butanol. The invention also relates to an air fragrance dispensing device of the wick type using such aqueous composition in which the evaporation rate of the fragrance is controlled to dispense the fragrance into the surrounding environment over extended periods of time, as well as into small or large areas.

2. Description of the Prior Art And Problem to be Solved

Conventional wick type air fresheners for dispensing air freshening fragrances from aqueous compositions include three essential components: (1) a reservoir containing the aqueous air freshening fragrance composition; (2) a diffuser or emanating surface from which the fragrance can evaporate into the surrounding environment; and (3) a wick which draws the fragrance composition via capillary action from the reservoir to the diffuser. In some of the wick type dispensers, the wick and the diffuser may be combined into a single molded unit to provide the same functions as the separate wick/diffuser units.

As described in U.S. Pat. No. 4,663,081, the aqueous fragrance mixture may be a true solution, a colloidal solution or a microemulsion, of the fragrance (e.g. perfume). However, since most of the fragrances used as air fresheners are water-insoluble oils or solids, it is generally necessary to include co-solvent and/or surface active agent, usually both co-solvent and surface active agent. The surface active agent is required to solubilize the fragrance in water, and is often present in amounts as high as 10 to 15% or more, by weight, based on the total composition. Since the surfactants, which are most typically anionic in nature, such as alkyl benzene sulfonates, e.g. sodium dodecyl benzene sulfonate, and sodium alkyl sulfates, e.g. sodium lauryl sulfate, or sometimes nonionic, such as ethoxylated alkyl phenols, e.g. ethoxylated nonyl phenol, are themselves substantially non-volatile, they do not evaporate or volatilize from the diffusing surface such that the concentration of the surface active agent on the diffusing surface gradually increases. The surface active agent also tends to clog the capillary wick. Therefore, the surface active agents impede the diffusion of the fragrance in the wick and prevent effective evaporation of the fragrance from the diffusing surface. Consequently, the fragrance which is trapped in the wick and in or on the diffuser, tends to deceive the consumer into believing that the product is still working even after substantially no more fragrance evaporation is taking place. Often, as much as 5 to 25% or more of the original fragrance mixture consisting predominantly of surface active agent and fragrance remains trapped in the diffuser and wick.

Where co-solvents such as ethanol or isopropanol are used, several additional technical problems occur. Co-solvents such as ethanol have a low flash point and, therefore, substantial amounts (e.g. 3 to 15% by weight of the total composition) of flame retardants must be added to the fragrance mixture at additional cost but without enhancing performance (see e.g. U.S. Pat. No. 4,810,690 for use of dimethyl methyl phosphonate as flame retardant for ethanol co-solvent). Some co-solvents also tend to present toxicity problems.

In addition, co-solvents such as ethanol, propanol, etc., tend to evaporate during the initial stages of use, heightening initial fragrance perception, but as fragrance and surface active agent levels begin to become more concentrated the fragrance perception begins to drop off.

For dispensing air freshening fragrance into larger areas or high traffic locations, such as offices, public bathrooms and the like, it is customary to provide a fan blowing on the diffuser surface to facilitate and promote evaporation and fragrance dispersion into the ambient atmosphere. For fragrance solutions using co-solvents and/or surfactants, the fan action preferentially increases co-solvent evaporation rates and exacerbates surfactant clogging of wick and diffuser by drying the aqueous mixture. Also, high surface active agent and co-solvent levels have led to an additional problem of warping of high density polyethylene (HDPE) fragrance reservoirs and delamination of heat sealed polyethylene/aluminum foil covers.

In the aforementioned U.S. Pat. No. 4,663,081 patentees disclose the use of diethylene glycol monobutyl ether (DEGMBE) as a fragrance solubilizer in an aqueous based liquid perfume composition which is substantially free of surface active agent. Patentees report that other glycol ethers, such as diethylene glycol monoethyl ether, propylene glycol monobutyl ether, propylene glycol monoethyl ether and the like, evaporate too rapidly or too slowly, and/or tolerate only very small amounts of water. In contrast DEGMBE is stated to have mid-range volatility and the capacity to tolerate far larger amount of water at a specified perfume concentration than any of the other glycol ethers.

However, while improved results may be achieved using DEGMBE as a perfume or fragrance solubilizer, it has been found that, especially at high levels of fragrance, for example 15 to 20%, surface active agents are required to obtain clear homogeneous fragrance solutions with consequent reduction in total fragrance evaporation as described above. In addition, for large scale commercial production, there is an additional problem in that DEGMBE partially degrades to form peroxide when stored in its shipping container and the peroxide present in the DEGMBE tends to oxidize and degrade the fragrance.

SUMMARY OF THE INVENTION

Accordingly, it is an object of the invention to provide aqueous fragrance compositions suitable for use in wick type air fresheners which avoid the above noted problems.

It is another object to provide aqueous fragrance compositions which are economical to produce and have good safety characteristics, including low toxicity and low flammability.

Another object of the invention is to provide aqueous fragrance compositions wherein the evaporation rate is regulated to within a predetermined period of time during which at least substantially all of the fragrance is effectively evaporated into the surrounding environment.

Another and related object of the invention is to provide aqueous fragrance compositions having a controllable evaporation rate and which permit effective utilization of the fragrance in a wick type air fragrance dispenser (air freshener).

Still another object of the invention is a wick type air fragrance dispenser using the invention aqueous fragrance composition and which can be satisfactorily adapted for industrial or domestic applications, including means, such as a fan, to promote fragrance evaporation and diffusion into the surrounding environment.

These and other objects of the invention which will become more readily apparent from the following detailed description and specific embodiments have been accomplished based on the discovery that 3-methyl-3-methoxy butanol having the formula $CH_3OC(CH_3)_2CH_2CH_2OH$ or the esters thereof (hereinafter often referred to as MMB and MMBE, respectively) are highly effective evaporation rate regulators for aqueous fragrance compositions and can form clear homogeneous aqueous fragrance mixtures over a wide range of concentrations of water, fragrance and MMB or MMBE, without requiring surface active agent or co-solvent.

Accordingly, the present invention provides, in one aspect thereof, an aqueous composition for controlled evaporation therefrom of a fragrance. The composition contains as essential ingredients water, fragrance, and an evaporation regulating and fragrance solubilizing amount of 3-methyl-3-methoxy butanol or an ester thereof.

In a second aspect, the invention provides an air fragrance dispenser of the wick type. The dispenser includes a reservoir containing an aqueous solution of a fragrance and an evaporation regulating and solubilizing effective amount of 3-methyl-3-methoxy butanol or an ester thereof; a diffuser surface from which said fragrance can evaporate and diffuse into the surrounding environment; and wick means associated with the aqueous solution and with the diffuser surface whereby the aqueous solution is transported via the wick to the diffuser surface to allow the fragrance to evaporate therefrom into the surrounding environment.

In a specific embodiment, the air fragrance dispenser is used with a fan arranged to blow air over the diffuser surface or other means, e.g. heat, to promote the diffusion of the evaporated fragrance throughout the surrounding environment and is especially useful in large rooms, industrial areas, and highly trafficked rooms, such as public restrooms and the like.

DETAILED DESCRIPTION OF INVENTION AND PREFERRED EMBODIMENTS

The aqueous compositions of this invention can be applied to virtually any of the various types and forms of fragrances previously used or suitable for administering into the ambient atmosphere for the purpose of providing a freshened or scented ambience. Thus, the fragrance may be selected from light oils, such as mint, citrus, pine, fruity, or spicy fragrances, to more viscous or heavy oils or solids, such as floral, powdery or woody scents. The percentage of fragrance will depend on such factors as volatility, strength, and cost. Whereas, conventional wick type air fresheners with aqueous fragrance mixtures have been effectively limited to fragrance concentrations of from about 1 to about 10% by weight, usually only about 5% by weight, at most, the aqueous compositions of this invention can be effectively used in wick type fragrance dispensers with fragrance levels as high as 30%, especially up to about 20%, for example from about 1 to 30% by weight, especially from 3 to 20% by weight, and preferably from about 5 to 20%, by weight of the total composition. Especially satisfactory results, especially for industrial air fresheners for large areas, have been achieved with 15% or 20% of fragrance.

Aqueous solutions which are characterized by their clarity and homogeneity and containing these elevated levels of fragrance are achieved, without requiring any surface active agents or co-solvents, by the presence in the aqueous solution of 3-methyl-3-methoxy butanol (MMB) or its ester (MMBE) in an amount effective to solubilize the fragrance and control its evaporation rate from the aqueous solution.

As a preferred example of the ester, mention can be made of the acetate of MMB. Both MMB and its acetate are commercially available from Kuraray Co. Ltd of Osaka, Japan, and is available in the United States from Chugai Boyeki (America) Corp. of New York, N.Y. MMB, has the structural formula

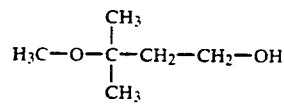

and is a chemical structural isomer of ethylene glycol monobutyl ether (EGMBE). MMB has previously been used for its solvent action in paints and inks and for various kinds of cleaners and polishes.

In addition to the acetate ester, other liquid aliphatic carboxylic acid esters of MMB, such as formate, propionate, and butyrate, may also be used.

For any given level of fragrance, the amount of MMB or MMBE necessary to provide a clear and homogeneous solution in water can be readily determined and usually the minimum amount of the solubilizer will be selected consistent with the desired rate of evaporation of fragrance and the economic benefit of maximizing water content.

For instance, for a wide variety of light to viscous oily fragrances clear and homogeneous aqueous solutions have been obtained with satisfactory evaporation rates using 15 parts fragrance, 60 parts MMB and 25 parts water without any surface active agent or co-solvent. For lower fragrance levels, such as 5%, clear and homogeneous aqueous mixtures have been obtained with 5 parts fragrance, 45 parts MMB and 50 parts water. For more concentrated solutions, somewhat higher MMB levels will be used. For instance, clear and homogeneous aqueous solutions can be obtained with 20% fragrance, 65% MMB and 15% water. As used herein "homogeneous" means the absence of phase separation and "clear" means no suspended particles visible with the naked eye, e.g. no visible oil droplets.

These minimum amounts of MMB, for any given fragrance level, may vary somewhat depending on the particular fragrance which may be more or less soluble in water and/or in MMB. However, the necessary amount may be easily determined by routine experimentation simply by preparing the aqueous fragrance mixture and observing the mixture for any phase separation or haziness or cloudiness. If either of these conditions are observed additional MMB or its ester should be added. Generally, however, for a wide range of fragrances the proportions given above for 5%, 15% and 20% fragrance levels will provide clear and homogeneous aqueous solutions. For intermediate fragrance levels or fragrance levels above or below these ranges suitable amounts of MMB or its ester may be routinely determined.

In addition to clarity and homogeneity, the aqueous fragrance solutions with MMB or its ester present at at least the minimum solubilizing effective amount will also exhibit a controlled rate of fragrance evaporation suitable for fragrance release over a minimum period of about 2 weeks and preferably over a period of from about 2 weeks to 90 days, especially from 20 to 45 days, 4 weeks or 30 days being a typical desired duration acceptable to the consumer.

If the evaporation rate is too fast or too slow, evaporation rate modifiers may be added to the aqueous fragrance solution. For instance, with some commercial type or residential type units which include a blower or fan to speed up evaporation of the fragrance from the diffuser surface and increase the rate and extent of diffusion and dispersion of the evaporated fragrance into the surrounding atmosphere, volatilization and evaporation of the more highly volatile fragrance types, such as citrus or mint, may reach as high as 97 to 98% depletion in as few as 15 days. The evaporation rate may, if desired, be decreased by addition of small amounts, such as from about 0.1 to about 5%, especially from about 1 to 3%, of a co-solvent. Dipropylene glycol is a preferred co-solvent for this purpose and is effective to slow fragrance evaporation to 30 days without loss of odor perception.

More generally, it may often be desirable to retard the rate of evaporation of the volatile fragrance regardless of the mechanical construction of the packaging or structural components of the fragrance dispensing device. In such case, any of the common perfumery solvents may be added to the aqueous fragrance composition. In addition to dipropylene glycol mentioned above, other typical evaporation rate retarding solvents, such as, for example, diethyl phthalate, benzyl alcohol, benzyl benzoate, propylene glycol, glyceryl triacetate (triacetin) and the like, may be used in amounts which may generally range from about 0.1 to about 5%, preferably from about 0.4 To 3%, by weight of the composition. The preferred organic solvents will be at least partially soluble in, or have an affinity to water. It is also preferred to premix the organic solvent with the MMB or MMBE, and fragrance, prior to the addition of water.

Conversely, for less volatile ("heavy") fragrances, such as some floral scents, the evaporation rate may be too slow for some uses, such as 45 to 60 or more days. In this case too, co-solvents which accelerate evaporation rate can be added to the composition. For example, it has been found that small amounts of ethanol, such as from about 5 to 30 weight percent, especially 5 to 15 weight percent, can accelerate fragrance evaporation to the ideal 30 day period. Surprisingly, in the MMB or MMBE system of this invention, the use of ethanol does not have a significantly notable effect of altering the degree of fragrance perception over the ideal 30 day period as is observed with conventional ethanol-surface active agent-aqueous fragrance compositions. Isopropanol can also be used to accelerate evaporation rate. In those cases where use of the alcoholic solvent is undesirable, the evaporation rate may also be accelerated by increasing the water content of the composition.

Accordingly, it can be appreciated that the present invention provides an easy and inexpensive technique for formulating aqueous fragrance compositions which may include low or high fragrance concentrations and which can provide low or high fragrance concentrations and which can provide easily adjustable rates of evaporation when the composition is exposed to the ambient surroundings.

As previously described, the presence of surface active agents in the aqueous fragrance solution is undesirable since the surface active agents tend to clog the wick and diffuser surface to effectively block fragrance evaporation. Accordingly, the compositions of this invention will preferably be free of any added surface active agent. However, it is common practice in the fragrance industry to formulate fragrances with small amounts of surface active agents. Such small amounts of surface active agents, which may account for up to about 3% by weight, preferably up to about 1% by weight, of the total aqueous fragrance composition, can be included in the composition without any significant loss of fragrance utilization. Accordingly, as used herein and in the appended claims, any reference to "substantially free of surface active agent" should be understood to allow the presence of surface active agent normally present in the fragrance being used and any additional surface active agent in an amount which would not result in clogging of the wick or diffuser to such an extent as resulting in more than about 2%, preferably more than about 0.8% by weight of the original weight of fragrance in the composition remaining as residue in the wick and diffuser when the aqueous fragrance solution is exhausted from the dispenser reservoir. It is most preferred that no additional surface active agents beyond any which may already be present in the fragrance be added to the invention compositions.

The aqueous fragrance solutions of this invention may be used with any construction of an air fragrance dispenser. One preferred type of dispenser typically comprises a housing or container which includes a reservoir or receptacle, usually at the bottom of the housing, in which the solution is stored, a diffuser surface from which the fragrance evaporates and is dispensed (by diffusion and/or convection; with or without the assistance of any blower or fan, heating device or other evaporation rate promoting means) into the surrounding environment, and wick means associated with both the diffuser surface and aqueous solution whereby the aqueous solution is drawn via capillary action through the wick to the diffuser surface. Usually a cover is provided for totally or partially covering the diffuser surface to partially or completely isolate the diffuser surface from the atmosphere. In some dispensers, the wick and the diffuser surface may be combined into a single molded unit of absorbent material, such as cellulose or other absorbent, water-resistant paper material, or porous polyethylene, polypropylene, or other synthetic polymeric material, or foam or other absorbent materials. As described in the aforementioned U.S. Pat. No. 4,663,081, it is often convenient to form the wick and diffuser surface (emanator surface) as an integral strip of cellulosic material, e.g. absorbent paper, which may have a narrow region forming the wick and dipping into the reservoir and a broader region forming the diffuser which will typically protrude from the dispenser housing. The MMB and MMBE solubilizers and evaporation rate regulators are non-reactive with most plastic materials, such as polyvinyl chloride (P.V.C.) resins, polyolefins, such as low or high density polyethylene, polyesters, such as polyethylene terephthalate, and phenolic resins. Any of these plastic materials may conveniently be used to form the dispenser housing, including the reservoir and container cover.

When the dispenser is to be used as an air freshener for larger rooms or public areas such as in public restrooms, building lobbies, retail store and office spaces and the like, it is often used in combination with a fan unit which will blow air over the diffuser surface to promote evaporation rates and increase the effective area of fragrance diffusion/convection and perception. The fan or blower may be incorporated in the dispenser housing above, below or along side of the fragrance reservoir to form an integral unit or it may be provided separately from the fragrance dispenser. The fan may be battery powered or may operate off of AC current. A battery powered fan is convenient for disposable dispensers whereas an AC powered fan may be more convenient for fragrance dispensers with refillable reservoirs, although here too, battery powered units offer the advantage of mobility and safety. Typical constructions of suitable fan/blower assisted and/or heating means assisted air fragrance dispenser devices are shown in the following representative U.S. patents, the disclosures of which are incorporated herein, in their entirety, by reference thereto: heated cartridge type: 4,629,604, 4,695,434, 4,695,434, and 4,556,539, all to Donald Spector; 2,931,880 —Yaffe, 4,631,387 —Glucksman, and 4,214,146 —Schimansk; lamp or light bulb heated: 2,942,090 —Diehl, 3,959,642 —Turro, 2,501,496 —Cartwright, and 4,346,059 —Spector; fan/blower assisted: 4,166,087 —Cline, 4,102,656 —Koritz, 3,993,444 —Brown, 4,229,415 —Bryson, and 4,078,891 —Madjar; miscellaneous types: 4,140,147 —Neuwald, et al., 2,585,106 —Frank, and 3,872,280 —Van Dalen.

While wick type air fresheners with large diffusing surfaces constitute a preferred embodiment of the air fresheners of this invention, the aqueous fragrance solutions may also be used with beneficial results in various other conventional air freshener devices, such as impregnated pads, aerosol and pump activated sprayers, pomanders, potpourri flowers, and the like. In addition, the aqueous fragrance solutions can also be used in a wide variety of products other than room fresheners, such as, fragranced printing and writing inks, odor eliminating products, combination hard surface cleaning and air freshening products, e.g. toilet cleaning and deodorizing products, carpet freshening products, laundry and other cleaning products, mineral, earth and clay-based products used for deodorizing, sawdust and wood shaving deodorizers and the like. Other types of products, such as personal care products, e.g. toiletries, perfumes, colognes, after shave products, etc., can also be formulated with the aqueous fragrance compositions of this invention.

In view of the broadly diverse applications, the term "fragrance" as used herein, and in the appended claims, should be construed, unless the context indicates otherwise, to include not only perfumes and other volatile essential oils and aromatic fragrances, but also volatile deodorizing, disinfecting and other chemically reactive volatile compounds which can interact with malodors or mask malodors, and for which the solubility in water is increased in the presence of MMB or MMBE. It is also within the scope of the invention to use the aqueous fragrance solution in the form of a paste or gel by addition thereto of conventional thickeners and/or gelling agents, such as, for example, natural or synthetic gums, rubbers, polymers or other organic substances, e.g. guar gum, carboxymethyl cellulose, polyvinylpyrrolidone, polyacrylates, and the like. Inorganic thickeners and gelling agents, such as silicates, stearates, and the like can also be used. The aqueous fragrance solutions may also be conveniently packaged in aerosol or pump type dispensers for spray applications into the environment. The aqueous fragrance solutions may also be impregnated in absorbent pads and foams for use as such or in dispensers in which the dispenser housing has one or more openings, which may be adjustable in size between fully opened and fully closed positions, e.g. of the type shown in U.S. Pat. Nos. 4,361,279 —Beacham, 4,371,571 —Hirvela, and 3,823,873 —Miller, Jr., et al., the disclosures of which are incorporated herein by reference thereto.

Accordingly, in its broadest aspect, the air fragrance dispenser for dispensing a volatile fragrance or other air-improving or air sanitizing or air freshening substance into the surrounding environment will include a storage compartment, which may be a reservoir or container for holding a liquid, or an absorbent or impregnatable pad or foam (e.g. cellulosic, polyurethane, etc.) capable of releasably holding or absorbing the aqueous fragrance solution, and the aqueous fragrance solution stored or absorbed or impregnated therein or thereon. Furthermore, the aqueous solution may be present in pure liquid form or as a thickened paste or gel.

In order to further exemplify and demonstrate the advantages and specific embodiments of the invention, the following non-limitative, representative examples are presented.

EXAMPLE 1

In order to test the effectiveness of MMB as a fragrance solubilizer, several different fragrances ranging from light to heavy in nature, including mint, spice and floral fragrances, were mixed with water at 5% and 15% fragrance levels, in a transparent polyethylene container and the appearance was observed. Similar results were obtained for each of the fragrance types and are reported below in Table 1.

From the results reported in Table 1, it is seen that clear and homogeneous solutions with 15% fragrance require more than about 55% of MMB, such as about 58% MMB. For a fragrance level of 5% only about 45% of MMB is required to achieve a clear and homogeneous aqueous solution. The data in Table 1 also shows that water is not necessary to achieve clear and homogeneous compositions. However, non-aqueous formulations are generally not economically attractive although they may be useful in certain types of applications or environments. It is also conceivable that the 2-component fragrance/MMB (or MMBE) compositions can be sold as a concentrate for dilution with water before adding to the reservoir or before use, for example, to minimize shipping weight.

TABLE 1

| | Fragrance Solubility in Water with MMB | | | | | | | | | | | | | |
|---|---|---|---|---|---|---|---|---|---|---|---|---|---|---|
| | Amount (wt %) | | | | | | | | | | | | | |
| Fragrance | 15 | 15 | 15 | 15 | 15 | 15 | 5 | 5 | 5 | 5 | 5 | 5 | 5 | 5 |
| MMB | 85 | 75 | 65 | 60 | 55 | 50 | 95 | 90 | 80 | 70 | 60 | 50 | 45 | 40 |
| Water | — | 10 | 20 | 25 | 30 | 35 | — | 5 | 15 | 25 | 35 | 45 | 50 | 55 |
| Solubility | C&H | C&H | C&H | C&H | Hz&H | Hz&S | C&H | C&H | C&H | C&H | C&H | C&H | C&H | Hz&S |

C = Clear
H = Homogeneous
Hz = Hazy/Cloudy
S = Phase Separation

EXAMPLE 2

The evaporation rate regulating effect of MMB was tested with three different fragrances using 15% fragrance, 60% MMB and 25% water in a wick type dispenser unit with a fan attachment. With the fan in continuous operation blowing over the diffuser surface, the odor perception in a 12 foot by 20 foot bathroom and the weight loss of the total composition from the dispenser were determined at the end of 1, 2, 3 and 4 weeks. Odor perception is reported in Table 2 as an average score of from 10 to 15 panelists given on a rating scale of 0 to 5 (0-no odor, 1-weak, 2-slight, 3-strong, 4-moderately strong, 5-very strong). Weight loss is reported in Table 2 as a percent calculated using the following formula:

$$\text{Weight loss } (\%) = \frac{W_o - W_t}{W_o} \times 100$$

where
$W_o$ = initial weight of dispenser unit including aqueous fragrance solution and
$W_t$ = remaining weight at time t of dispenser unit including aqueous fragrance solution in reservoir, wick and diffuser surface.

TABLE 2

| | Week 1 | | Week 2 | | Week 3 | | Week 4 | |
|---|---|---|---|---|---|---|---|---|
| Fragrance | Odor Perception | Wt. Loss (%) | Odor Perception | Wt Loss (%) | Odor Perception | Wt. Loss (%) | Odor Perception | Wt. Loss (%) |
| #1 | 3.5 | 34 | 3.5 | 55 | 3.5 | 73 | 3.0 | 95 |
| #2 | 3.1 | 37 | 3.1 | 56 | 3.0 | 75 | 3.0 | 97 |
| #3 | 4.0 | 40 | 3.5 | 61 | 3.5 | 79 | 3.5 | 98 |

From the results of Table 2, it is seen that the aqueous fragrance solution is effectively dispensed at a uniform linear rate with near total fragrance exhaustion at the end of a 30 day period with continuous fan operation and with nearly uniform odor perception over the 4 week dispensing period.

EXAMPLE 3

This example shows the evaporation regulating effect of MMB as compared to DEGMBE and other glycol ethers. In this example, aqueous fragrance solutions were prepared with 10% fragrance, 60% solubilizer and 30% water. The tests were carried out using both a light mint fragrance and a heavy (sappy) floral fragrance. The evaporation rates were measured by absorbing 5 grams of the test aqueous solution on an absorbent cellulose pad placed in a petri dish at ambient temperature environment (70° F.)

The results are reported in Table 3.

TABLE 3

| Solubilizer | Evaporation Rate (gm/day) |
|---|---|
| MMB | 2.65 |
| DEGMBE | 1.5-1.7 |
| Butyl Cellosolve | 1.5-1.7 |
| TPGMME | 1.5-1.7 |

WHAT IS CLAIMED IS:

1. An aqueous composition for controlled evaporation therefrom of a fragrance comprising water, fragrance, and an evaporation regulating and fragrance solubilizing amount of 3-methyl-3-methoxy butanol or an ester thereof.

2. The composition of claim 1 in which the fragrance is present in an amount of 1% to 30% by weight.

3. The composition of claim 1 in which the fragrance is present in an amount of 3% to 20% by weight.

4. The composition of claim 1 in which water is present in an amount of 5% to 60% by weight.

5. The composition of claim 1 which comprises 3-methyl-3-methoxy butanol or its ester in an amount of 40% to 90% by weight.

6. The composition of claim 1 which comprises 3-methyl-3-methoxy butanol or its ester in an amount of 45% to 65% by weight.

7. The composition of claim 1 which comprises from about 20% to about 50% by weight of water; from about 5% to about 20% by weight of fragrance; and from about 45% to about 65% by weight of 3-methyl-3-methoxy butanol or its ester.

8. The composition of claim 1 which comprises from about 20% to about 30% by weight of water; from about 10% to about 20% by weight of fragrance; and from about 55% to about 65% by weight of 3-methyl-3-methoxy butanol or its ester.

9. The composition of claim 8 which is substantially free of surface active agent.

10. The composition of claim 1 which is substantially free of surface active agent.

11. An air fragrance dispenser which comprises a reservoir containing an aqueous solution of a volatile fragrance and an evaporation regulating and fragrance solubilizing effective amount of 3-methyl-3-methoxy butanol or an ester thereof, a diffuser surface from which said fragrance is dispensed into the surrounding environment; and wick means associated with said aqueous solution and said diffuser surface whereby in operation said aqueous solution is transported via said wick to said diffuser surface to allow said fragrance to evaporate therefrom for dispensing into said surrounding environment.

12. The air fragrance dispenser of claim 11 further comprising means for promoting evaporation of fragrance from the diffuser surface.

13. The air fragrance dispenser of claim 11 wherein said aqueous solution is present in said reservoir absorbed on an absorbent solid material.

14. The air fragrance dispenser of claim 11 wherein said aqueous solution is present in said reservoir in liquid form.

15. The air fragrance dispenser of claim 12 wherein the aqueous solution contains sufficient amount of fragrance and 3-methyl-3-methoxy butanol or its ester to be substantially fully depleted from said reservoir and from said dispenser over a period of no less than 20 days and no more than 90 days when said fan is operated continuously.

16. The air fragrance dispenser of claim 12 wherein said means comprises a fan.

17. The air fragrance dispenser of claim 13 wherein said means comprises means for heating the aqueous solution.

18. An air fragrance dispenser comprising a storage compartment and within said storage compartment an aqueous solution of a volatile fragrance and an evaporation regulation and fragrance solubilizing effective amount of 3-methyl-3-methoxy butanol or an ester thereof.

19. The air fragrance dispenser of claim 16 further comprising a housing for said storage compartment, said housing having at least one opening providing an outlet for volatile fragrance evaporated from said aqueous solution.

20. The air fragrance dispenser of claim 16 wherein said storage compartment comprises an absorbent material and wherein the aqueous solution is releasably absorbed by said absorbent material.

21. The air fragrance dispenser of claim 17 which further comprises wick means having one portion thereof in contact with the aqueous solution and another portion thereof in proximity to said at least one opening to promote evaporation of said volatile fragrance in proximity to, and for dispensing through, said at least one opening.

* * * * *